(12) United States Patent
Potisek et al.

(10) Patent No.: US 9,382,373 B2
(45) Date of Patent: Jul. 5, 2016

(54) CURABLE COMPOSITIONS AND THERMOSETS PREPARED THEREFROM

(71) Applicant: Blue Cube IP LLC, Midland, MI (US)

(72) Inventors: Stephanie L. Potisek, Houston, TX (US); Michael J. Mullins, Houston, TX (US)

(73) Assignee: BLUE CUBE IP LLC, Midland, MI (US)

(*) Notice: Subject to any disclaimer, the term of this patent is extended or adjusted under 35 U.S.C. 154(b) by 0 days.

(21) Appl. No.: 14/423,864

(22) PCT Filed: Oct. 25, 2013

(86) PCT No.: PCT/US2013/066738
§ 371 (c)(1),
(2) Date: Feb. 25, 2015

(87) PCT Pub. No.: WO2014/066718
PCT Pub. Date: May 1, 2014

(65) Prior Publication Data
US 2015/0183923 A1   Jul. 2, 2015

Related U.S. Application Data

(60) Provisional application No. 61/718,768, filed on Oct. 26, 2012.

(51) Int. Cl.
| | | |
|---|---|---|
| C08G 59/68 | (2006.01) | |
| C08F 2/46 | (2006.01) | |
| B29C 71/04 | (2006.01) | |
| C08G 61/04 | (2006.01) | |
| C08G 59/02 | (2006.01) | |
| C07D 301/03 | (2006.01) | |
| C07D 303/04 | (2006.01) | |
| C08G 59/24 | (2006.01) | |
| C08G 59/32 | (2006.01) | |
| C08K 5/1515 | (2006.01) | |
| C09D 163/00 | (2006.01) | |
| C09J 163/00 | (2006.01) | |

(52) U.S. Cl.
CPC .............. *C08G 59/02* (2013.01); *C07D 301/03* (2013.01); *C07D 303/04* (2013.01); *C08G 59/24* (2013.01); *C08G 59/3218* (2013.01); *C08K 5/1515* (2013.01); *C09D 163/00* (2013.01); *C09J 163/00* (2013.01)

(58) Field of Classification Search
CPC .... C08G 59/02; C08G 59/24; C08G 59/3218; C09J 163/00; C09D 163/00; C07D 301/03; C07D 303/04
USPC .................. 522/31, 6, 1, 71, 189, 184; 520/1
See application file for complete search history.

(56) References Cited

U.S. PATENT DOCUMENTS

| | | | | |
|---|---|---|---|---|
| 3,476,693 A * | 11/1969 | Mango | ............... | C07D 303/04 156/330 |
| 2009/0258962 A1* | 10/2009 | Martz | ............... | C08G 18/2063 522/53 |
| 2015/0225359 A1* | 8/2015 | Potisek | ............... | C07D 301/03 549/512 |

FOREIGN PATENT DOCUMENTS

| | | |
|---|---|---|
| DE | 1160850 B | 9/1964 |
| GB | 1185137 A | 3/1970 |
| JP | 2011195483 A | 6/2011 |
| TW | 201202291 A1 | 1/2012 |
| TW | 201219439 A1 | 5/2015 |
| WO | WO 2011114935 A1 | 9/2011 |
| WO | WO 2012020661 A1 | 2/2012 |
| WO | WO 2014066718 A1 | 5/2014 |

OTHER PUBLICATIONS

Crivello and Dietliker, in Chemistry & Technology of UV & EB Formulation for Coatings Inks & Paints, vol. 3, 1991, p. 329.
May, "Epoxy Resins Chemistry & Technology," 2nd Edition, Marcel Dekker, 1988, pp. 683-693, pp. 735748, pp. 758-782, 790-813.
United States Patent and Trademark Office, Non-Final Office Action for U.S. Appl. No. 14/423,864 dated Dec. 10, 2015.
European Patent Office, International Preliminary Report on Patentability for PCT/US13/066738 dated Apr. 28, 2015.
European Patent Office, Written Opinion of the International Searching Authority for PCT/US13/066738 dated Apr. 26, 2015.
European Patent Office, International Search Report for PCT/US13/066738 dated Dec. 19, 2013.
(Continued)

*Primary Examiner* — Ling Choi
*Assistant Examiner* — Jessica E Whiteley
(74) *Attorney, Agent, or Firm* — Polsinelli PC

(57) ABSTRACT

A curable composition comprising (a) at least one low viscosity epoxide resin compound having the following chemical structure: (I) wherein $R_1$ and $R_2$ are hydrogen or a hydrocarbon group having from 1 to 20 carbon atoms, with the proviso that $R_1$ and $R_2$ are not both hydrogen, and (b) at least one curing agent or UV photoinitiator; and a thermoset prepared from the above curable composition.

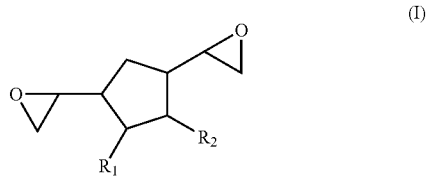

(I)

23 Claims, No Drawings

(56) References Cited

OTHER PUBLICATIONS

State Intellectual Property Office of People's Republic of China, First Office Action for Chinese Pat. App. No. 201380054146.8 dated Oct. 28, 2015.

State Intellectual Property Office of People's Republic of China, Search Report (English Translation) for Chinese Pat. App. No. 201380054146.8 dated Oct. 9, 2015.

\* cited by examiner

CURABLE COMPOSITIONS AND THERMOSETS PREPARED THEREFROM

FIELD

The present invention is related to curable epoxy resin compositions and thermosets prepared from the curable compositions or formulations.

BACKGROUND

As many epoxy industries develop, improvements are needed in the material properties of the epoxy resin thermosets. For example, thermosets with high glass transition temperatures, such as 200° C. and greater, are needed for use in the aerospace and the electrical laminates industry. In another example, UV stable and weatherable thermosets are needed for the coatings industry. In still another example, thermosets that are highly filled with thermally conductive or low coefficient of thermal expansion (CTE) fillers are needed for the semiconductor industry.

Typically, epoxide compounds are used alone, or in combination with other additives to form a desired curable formulation for various enduses. Frequently these formulations need to be low viscosity. Typical epoxy resins have viscosities at or above 10 Pa-s, which result in formulations with high viscosities that are difficult to process. Usually, the epoxide compound has to be diluted with a diluent to reduce the epoxide compound's viscosity and to provide a formulation with a processable viscosity before such epoxide resin formulation can be used. An epoxide compound having a low initial viscosity, for example below (0.3 Pa-s), before mixing with other additives, to prepare a curable composition or formulation would be an advantage in the industry because such an epoxide would (i) be useful in a wide range of applications, (ii) reduce manufacturing costs, and (iii) reduce the number of additives such as diluents needed for making the curable formulation processable.

In addition, an epoxide compound having a low volatility, for example below 0.000017 Pa before mixing with other additives, to prepare a curable composition or formulation would be an advantage in the industry because such an epoxide with low volatility would (i) prevent evaporation of the epoxide, since a high volatility epoxide can cause void formation in a thermoset; and (ii) prevent evaporation of the epoxide and consequently a change in the epoxide hardener ratio, which can cause changes in the thermomechanical and physical properties of a thermoset such as modulus, glass transition temperature (Tg), and moisture uptake.

SUMMARY

One aspect of the present invention is directed to an epoxy curable formulation having a sufficiently low viscosity and low volatility to process the formulation more easily and more efficiently into thermoset resin products for use in a wider range of various applications and enduses.

For example, in one embodiment of the present invention a curable composition includes at least one low viscosity epoxide resin compound comprising an epoxide compound having the following chemical structure:

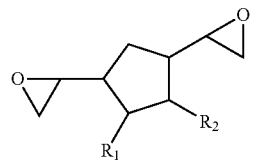

wherein $R_1$ and $R_2$ comprises hydrogen or a hydrocarbon group having from C1 to about C20 carbon atoms; with the proviso that $R_1$ and $R_2$ are not both hydrogen.

For example, in another embodiment of the present invention a curable composition includes: (a) at least one low viscosity epoxide resin compound comprising an epoxide compound having the following chemical structure:

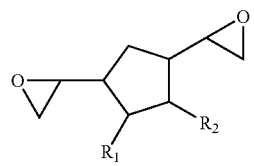

wherein $R_1$ and $R_2$ comprises hydrogen or a hydrocarbon group having from C1 to about C20 carbon atoms; with the proviso that $R_1$ and $R_2$ are not both hydrogen; and (b) at least one curing agent or photoinitiator.

In yet other embodiments, the above curable composition may include optional compounds, such as at least one catalyst, depending on the end use of the curable composition.

Still another embodiment of the present invention is directed to a thermoset prepared from the above curable composition.

The low viscosity epoxide resin compound of the present invention has a low viscosity (e.g., less than about 0.3 Pa-s) compared to standard epoxy resins (e.g., less than about 10 Pa-s). One of the advantages of using the low viscosity epoxide resin compound of the present invention is that formulations using the low viscosity epoxy resin will also exhibit a lower viscosity than those formulations prepared with a standard epoxy resin. Low viscosity formulations are advantageously used in end uses that require formulations with high filler loadings such as capillary underfill and composites.

It is known that standard epoxy resins that contain aromatic functionalities or aromatic groups, such as DVBDO, bis-A resins, bis-F resins, and phenolic novolacs, are typically not UV stable. Thus, cycloaliphatic resins that do not contain aromatic groups are usually used for applications requiring UV stability. Accordingly, another advantage of using the low viscosity cycloaliphatic epoxide resin compound of the present invention is the fact that the epoxide resin compound is cycloaliphatic and does not contain aromatic groups; such that when used in a curable composition, the present invention low viscosity cycloaliphatic epoxide resin compound without aromatic groups exhibits UV stability.

Additionally, the present invention low viscosity cycloaliphatic epoxide resin compound can be cured with a wide variety of hardeners including amines, anhydrides, cyanate esters, and phenolics. The flexibility to cure the low viscosity cycloaliphatic epoxide resin compound of the present invention with amines is advantageous because many important cycloaliphatic epoxies do not readily cure with amines. Accordingly, the curable composition of the present invention is unique and advantageous because of its combination of a cycloaliphatic resin that is UV stable and its curability with amines.

Still another advantage of the low viscosity composition of the present invention is that the epoxy resin used in the composition is not made using chlorine containing raw materials such as epichlorohydrin. Therefore, the resulting epoxy resin is free of chlorohydrin and chlorine impurities (i.e., "clean") and can be used in electronics applications requiring such clean epoxy resins.

The epoxy resins useful in the present invention are less volatile than conventional low viscosity epoxy resins. Thus, another advantage of the low volatility resin is that it can be used as a reactive diluent and in formulations that must exhibit low weight loss during cure.

Accordingly, the epoxy resin composition of the present invention includes (1) a low viscosity (e.g. less than about 0.3 Pa-s) resin, (2) a clean and halogen free (e.g. less than about 100 ppm chlorine) resin, (3) a cycloaliphatic resin that imparts UV stability, (4) a resin that exhibits low volatility (e.g. less than about 0.001 mmHg at 25° C.), and (5) a resin that provides thermosets that exhibit high glass transition temperatures (for example 270° C.).

DETAILED DESCRIPTION

One broad embodiment of the present invention is directed to providing a curable resin formulation or composition including (a) at least one low viscosity liquid epoxide compound such as DVHPTO; and a compound that allows the low viscosity liquid to cure under curing conditions. For example, the curable resin composition can include (b1) at least one curing agent such as an amine, or (b2) at least one UV photoinitiator. Other optional additives known to the skilled artisan can be included in the curable composition such as for example a curing catalyst and other additives for various enduse applications.

The low viscosity epoxide compound useful as component (a) in preparing a curable composition of the present invention may comprise, for example, a low viscosity liquid epoxy resin compound. For example, the low viscosity liquid epoxy resin compound useful in the present invention may include the epoxy compounds described in U.S. Provisional Patent Application Ser. No. 61/718,752, incorporated herein by reference.

In one embodiment, a broad scope of component (a) useful in the curable composition of the present invention includes for example a compound having the following general structure:

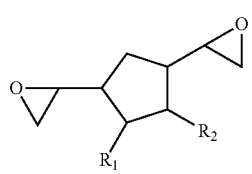

Structure (I)

wherein $R_1$ and $R_2$ comprises hydrogen or a hydrocarbon group having from C1 to about C20 carbon atoms and can be, but is not limited to cycloaliphatic, and bicyclic groups; with the proviso that $R_1$ and $R_2$ are not both hydrogen.

For example, in one embodiment, the above low viscosity epoxy compound may include DVHPTO, an epoxy having the structure as shown in Structure (II) as follows:

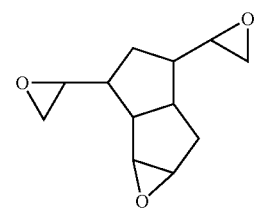

Sturcture (II)

For example, in another embodiment, the low viscosity epoxy compound may have the structure as shown in Structure (III) as follows:

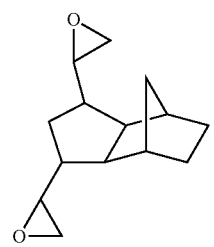

Structure (III)

For example, in another embodiment, the low viscosity epoxy compound may have the structure as shown in Structure (IV) as follows:

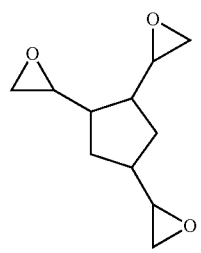

Structure IV

A process useful for preparing the low viscosity epoxide compound described above, such as DVHPTO, can include for example the process described in U.S. Provisional Patent Application Ser. No. 61/718,752. For example, the low viscosity epoxy resin, such as DVHPTO, useful for the curable composition of the present invention may be produced by reacting or epoxidizing 2,4-divinylbicyclo[3.3.0]oct-6-ene) [DVHP] with at least one oxidizing agent under reaction conditions to form an epoxide. The epoxide product prepared by the above process may be for example a epoxy compound having a viscosity of less than about 0.3 Pa-s and having the following general chemical structure (I):

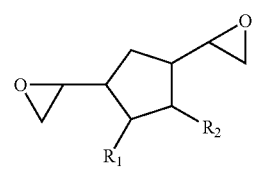

Structure (I)

where $R_1$ and/or $R_2$ can be, but are not limited to, a hydrocarbon group have from C1 to about C20 carbon atoms including for example aliphatic, cycloaliphatic, aromatic, and bicyclic groups. $R_1$ and $R_2$ can also be joined to form a cycloaliphatic or bicycloaliphatic ring. In another embodiment, the C1 to C20 carbon atoms of $R_1$ and $R_2$ may contain an oxirane ring attached to any one of the carbon atoms of the $R_1$ and/or $R_2$ groups.

The process for preparing DVHPTO may include for example a two-step process, wherein as a first step includes providing a precursor DVHP; and then, as a second step, epoxidizing the DVHP under process reaction conditions to generate DVHPTO. The precursor DVHP used in the first step of the above two-step process may be synthesized by any synthesis process known in the art such as for example ethenolysis of DCPD as described in U.S. Provisional Patent Application Ser. No. 61/718,752. The above epoxidation second step can be carried out using various epoxidation processes. For example, one useful process can include reacting DVHP with an oxidant or oxidizing agent to form the DVHPTO epoxide compound of the present invention. In one embodiment, for example, the oxidant or oxidizing agent used in the above epoxidation second step of the above two-step process may include for example Oxone®; percarboxylic acids such as peracetic acid or meta-chloroperoxybenzoic acid; hydrogen peroxide catalyzed with acetonitrile, and mixtures thereof. Other epoxidation processes useful in the present invention are described in U.S. Provisional Patent Application Ser. No. 61/718,752.

The DVHPTO advantageously used in preparing the curable liquid formulation of the present invention has a low viscosity. For example, generally DVHPTO has a viscosity of less than about 0.3 Pa-s in one embodiment; from about 1.0 Pa-s to about 0.001 Pa-s in another embodiment, from about 0.5 Pa-s to about 0.01 Pa-s in still another embodiment, and from about 0.3 Pa-s to about 0.02 Pa-s in yet another embodiment, at 25° C. The viscosity of DVHPTO is much lower than standard liquid epoxy resins known in the art which typically are 10 Pa-s or higher.

The DVHPTO compound of the present invention is used to make a curable composition which, in turn, can be cured to form a thermoset.

The concentration of the liquid DVHPTO epoxy compound used in the curable composition of the present invention as the epoxy resin may range generally from about 5 weight percent (wt %) to about 99.5 wt % in one embodiment, from about 5 wt % to about 95 wt % in still another embodiment, and from about 5 wt % to about 90 wt % in yet another embodiment, based on the weight of the curable composition.

In general, the curing agent, component (b1), blended with the epoxy resin compound, component (a), to prepare the curable composition may comprise, for example, any conventional curing agent known in the art useful for including in a curable composition. The curing agent, (also referred to as a hardener or cross-linking agent) useful in the curable composition, may be selected from, for example, but are not limited thereto, anhydrides, carboxylic acids, amine compounds, phenolic compounds, cyanate ester compounds, or mixtures thereof.

Examples of curing agents useful in the present invention may include any of the co-reactive or catalytic curing materials known to be useful for curing epoxy resin based compositions. Such co-reactive curing agents include, for example, polyamine, polyamide, polyaminoamide, dicyandiamide, polymeric thiol, polycarboxylic acid and anhydride, and any combination thereof or the like. Other specific examples of co-reactive curing agent include diaminodiphenylsulfone, styrene-maleic acid anhydride (SMA) copolymers; and any combination thereof. Among the conventional co-reactive epoxy curing agents, amines and amino or amido containing resins and phenolics are preferred.

Specific examples of amine co-reactive curing agents useful in the composition of the present invention include aromatic amines such as methylene dianiline Also included are aliphatic amines such as xylylene diamine, aminoethanol, ethylene diamine, propylene diamine, diethylene triamine, triethylene tetramine, tetraethylene pentamine, aminated polyols such as Jeffamines (Huntsman trademark), cycloaliphatic amines such as isophorone diamine, bisparaaminocyclohexyl methane, and 1,2-diaminocyclohexane, piperidine, aminoethyl piperidine, "Mannich bases" derived from condensations of resoles with alkylene polyamines such as ethylene diamine and xylylene diamine. Other amines include for example amides and guanidines such as dicyandiamide.

Specific examples of phenolic curing agents useful in the composition of the present invention include bisphenols of the formula $HOC_6H_4-Z-C_6H_4OH$ where Z can be 2,2-propylidene, 1,1-ethylidene, 1,2-ethylidene, methylene, sulfone, and oxygen. Other specific examples include resorcinol, hydroquinone, naphthalenediol, phenolphthalein and polyphenols (novolacs) such as condensation products of phenols and bisphenols with formaldehyde and other aldehydes.

Specific examples of anhydride curing agents useful in the composition of the present invention include maleated hydrocarbon polymers such as maleated polybutadiene, copolymers of maleic anhydride with styrene, polyphthalic anhydrides, cycloaliphatic anhydrides such as nadic anhydride, methyl nadic anhydride, methyl hexahydrophthalic anhydride; and mixtures thereof.

Specific examples of cyanate ester curing agents include, but are not limited to bisphenol A cyanate ester; 1,1-bis(4-cyanatophenyl)ethane; novalac cyanate esters such as Primaset™ Pt-15; aromatic cyanate esters; w,3-dicyanatobenzene; tetramethyl-1,4-dicyanatobenzene; 1,3,5-tricyanatobenzene, and bis(4-cyantophenyl)ether.

Generally, the amount of the curing agent used in the curable composition of the present invention, may be for example, from about 5 wt % to about 95 wt % in one embodiment, from about 10 wt % to about 95 wt % in another embodiment; from about 15 wt % to about 95 wt % in still another embodiment; and from about 20 wt % to about 90 wt % curing agent in yet another embodiment.

In another embodiment, the curable composition of the present invention may comprise an ultra violet light (UV) curable composition which includes for example a photoinitiator compound in the composition. The resultant UV curable composition can be subjected to a source of UV light to cure the composition. For example, in one embodiment, the UV curable composition of the present invention can include (a) at least one low viscosity liquid epoxy resin compound, such as DVHPTO; and (b) a photoinitiator to provide a UV curable composition.

In one embodiment, the photoinitiators which may be used to achieve polymerization in the present invention can include diazonium salts, iodonium salts, aryl diazonium salts, aryl iodonium salts, arylsulfonium salts, diaryliodonium salts, triarylsulfonium salts, phenacylsulfonium salts, diaryliodosonium salts, triarylsulfoxonium salts, dialkylphenacylsulfonium salts, ferrocenium salts, dialkyl-4-hydroxyphenylsulfonium salts, allene-ion complexes and mixtures thereof. Typically, these salts contain complex metal halide or other non-nucleophilic ions such as $BF_4-$, $PF_6-$, $SbF_6-$, $AsF_6-$, $ClO_4-$, $CF_3SO_3-$, $(C_6F_5)_4B-$ and the like.

In one preferred embodiment, the photoinitiators useful in the present invention may include sulfonium salts of the formula Ar—C(O)CH$_2$S+R'R"X— wherein Ar is monocyclic or bicyclic aryl or substituted aryl, such as phenyl, naphthyl, biphenyl, anthracenyl, phenanthryl, or heterocyclic such as furanyl or thiophenyl; R' and R" are the same or different and are alkyl, cycloalkyl or aromatic, and x- is a non-nucleophilic anion as described above.

Examples of suitable photoinitiator salts useful in the composition of the present invention can include commercially available photoinitiators such as PP-33 available from Asahi Denka Kogyo K. K.; FC-509 available from Minnesota Mining and Manufacturing Company; UVE 1014 available from G.E.; CP-66 and CP-77 available from Asahi Denka Kogyo K. K.; SI-60L, SI-80L, SI-100L, and SI-110L available from Sanshin Chemical Industry Co., Ltd.; and CG-24-61 available from Ciba Geigy Ltd. Other cationic c photoinitiators useful in the present invention may also include commercially available photoinitiators such as CPI6992 and CPI6976 available from Aceto Corp. CPI6992 and CPI6976 comprise a mixed triaryl sulfonium hexafluorophosphate salt solution in propylene carbonate. Other examples of suitable photoinitiator salts usefuyl in the present invention may include the photoinitiator salts described in Crivello and Dietliker, in Chemistry & Technology of UV & EB Formulation for Coatings Inks & Paints, Vol. 3, 1991, page 329, the disclosure of which is hereby incorporated herein by reference.

Generally, the amount of photoinitiator used in the UV curable composition of the present invention may be for example, from about 0.01 wt % to about 10 wt % solids based on the weight of the epoxy compound or compounds in one embodiment, from about 0.1 wt % to about 10 wt % solids in another embodiment, and from about 0.5 wt % to about 5 wt % solids in still another embodiment.

As noted herein, one aspect of the present invention includes a UV curable composition containing the low viscosity epoxy compounds of the present invention and one or more photoinitiators for polymerization of the composition. Rapid and complete polymerization of the epoxy compounds can be achieved by irradiating the curable composition with an electron beam or x-ray dose on the order of 0.1 to 10 Mrad or ultraviolet radiation flux on the order of 10-30 mW/cm$^2$. Higher energy levels are also useful, especially when higher throughput speeds are desired or thicker masses of polymer are presented.

Photopolymerizable compositions containing the epoxy compounds of the present invention can also contain any of the other additives customary for such uses, in the amounts thereof adequate to enable the additive to perform its desired function. Such additives include photosensitizers, fillers, flow control agents, and the like. Examples of suitable materials for providing these functions abound in this field and are well known to those experienced in this field, and include the materials which are employed for those functions.

In one illustration of a UV curable composition wherein a UV photoinitiator is used, particularly in the enduse of a coating, the UV curable composition can include (a) a low viscosity liquid epoxy resin compound and (b) a UV photoinitiator. The coating formulation includes for example a low viscosity liquid epoxy resin compound in a concentration of from about 95 wt % to about 99.9 wt %; and a UV photoinitiator in a concentration of from about 0.01 wt % to about 5 wt %.

In preparing the curable resin composition of the present invention, optional compounds may be added to the curable composition of the present invention depending on the end use in which the curable composition will be used.

For example, compounds that are normally used in resin formulations known to those skilled in the art for preparing curable compositions and thermosets can be used in the present invention. The optional compounds may include for example compounds to enhance application properties (e.g. surface tension modifiers or flow aids), reliability properties (e.g. adhesion promoters), reaction rate, selectivity of the reaction, and/or lifetime.

Optional compounds that may be added to the curable composition of the present invention may include, for example, a cure catalyst (for example, imidazole, acid catalysts, ammonium blocked acid catalysts, quaternary amines, superacid catalysts, metal complexes) and such catalysts may be added to the formulation. Specific examples of catalysts suitable for use with the low viscosity epoxy compound of the present invention (such as DVHPTO) include imidazoles such as 1-methylimidazole, 2-methylimidazole, 2-phenylimidazole, 2,4-ethylmethylimidazole, tertiary amines such as triethylamine, benzyldimethylamine, dimethylaminomethyl phenol, tris(dimethylaminomethyl) phenol, acid salts of these tertiary amines; phosphines such as triphenyl phosphine; and mixtures thereof. Boric acid and borate derivatives such as trimethyl borate can be used in conjunction with the above catalysts to provide latency or extended pot life to the composition of the present invention. Any combination of one or more of the above compounds can also be used to facilitate the reaction of the novel epoxy resin compound with the curing agent when a curing agent is used in the composition.

Another optional compound useful in the present invention may include a solvent, such as for example, methyl isobutyl ketone, Dowanol® PM, cyclohexanone, toluene, methyl ethyl ketone or any combination thereof, to lower the viscosity of the formulation further than the inherent viscosity of the low viscosity epoxy compound, if desired.

Still another optional compound useful in the present invention may include another epoxy resin, i.e., a second epoxy compound different from the liquid epoxy resin component (a) such as for example, aromatic and aliphatic glycidyl ethers; cycloaliphatic epoxy resins; divinylarene dioxides such as divinylbenzene dioxide or any combination thereof, in addition to the liquid epoxy resin component (a) to form the epoxy matrix in the final curable formulation.

Other optional compounds useful for adding to the curable composition of the present invention may depend on the end use of the curable composition and may include other resins such as a phenolic resin, other curing agents, fillers, pigments, toughening agents, flow modifiers, adhesion promoters, diluents, stabilizers, plasticizers, catalyst de-activators, flame retardants, and mixtures thereof.

Specific examples of fillers useful for adding to the curable composition of the present invention may include talc, clay, calcium carbonate, silica, alumina, sand, silicon carbide, boron nitride, boron carbide, aluminum nitride, and mixtures thereof. For electrical and/or thermal conductivity, fillers such as carbon, graphite, carbon fibers, silver, copper, and aluminum may also be used.

In another embodiment of the present invention, a lower grade of DVHPTO, for example a DVHPTO containing a certain level of impurities (e.g. impurities such as diepoxides and monoepoxides) may optionally be used in addition to or as the low viscosity liquid epoxy resin compound of the present invention curable composition. While impurities found in a lower grade of DVHPTO may lower the glass transition temperature of the final composition, some enduses may withstand such lower glass transition temperatures.

Generally, the amount of other optional components, when used in the present invention, may be for example, from 0 wt % to about 95 wt % in one embodiment and from about 0.01 wt % to about 80 wt % in another embodiment.

The process for preparing the curable composition of the present invention includes admixing (a) at least one liquid epoxide compound of the present invention such as DVHPTO; (b) at least one curing agent such as an amine or at least one UV photoinitiator; and (c) optionally, other optional ingredients or additives as needed. For example, the preparation of the curable resin formulation of the present invention is achieved by blending, in known mixing equipment, the compound, and the curing agent, and optionally any other desirable additives. Any of the above-mentioned optional additives, for example a curing catalyst, may be added to the composition during the mixing or prior to the mixing to form the composition.

All the compounds of the curable formulation are typically mixed and dispersed at a temperature enabling the preparation of an effective curable epoxy resin composition having the desired balance of properties for a particular application. For example, the temperature during the mixing of all components may be generally from about room temperature (20-25° C.) or higher if necessary to enable the preparation of an effective curable epoxy resin composition having the desired balance of properties for a particular application 0° C. to about 100° C. in one embodiment, and from about 20° C. to about 50° C. in another embodiment. Lower mixing temperatures help to minimize reaction of the epoxide and hardener in the composition to maximize the pot life of the composition.

The preparation of the curable formulation of the present invention, and/or any of the steps thereof, may be a batch or a continuous process. The mixing equipment used in the process may be any vessel and ancillary equipment well known to those skilled in the art.

In one embodiment, the use of the liquid epoxide compound of the present invention, such as DVHPTO, imparts improved properties to the curable composition and the final cured product over conventional glycidyl ether, glycidyl ester or glycidyl amine epoxy resin formulations. The unique combination of low viscosity of DVHPTO in the uncured state, and high Tg of the cured product prepared from DVHPTO, enables a formulator to apply new formulation strategies. In addition, the ability to cure the epoxy resin of the present invention with an expanded hardener range, offers the formulator significantly improved formulation latitude over other conventional types of epoxy resins such as cycloaliphatic epoxy resins. Furthermore, the lower vapor pressure of the liquid epoxide compound of the present invention compared to other low viscosity epoxy resins results in lower weight loss during cure in the curable composition, which prevents a negative affect on the final material properties that is known to occur with high weight loss during cure.

The process of the present invention includes curing the curable resin composition to form a thermoset or cured composition. In one embodiment, the curable resin composition can be cured under thermal curing conditions. For example, the process of curing of the curable composition may be carried out at a predetermined temperature and for a predetermined period of time sufficient to cure the composition; and the curing conditions may be dependent on the hardeners used in the formulation.

For example, the temperature for thermal cure of the formulation may be generally from about 10° C. to about 325° C. in one embodiment; from about 100° C. to about 300° C. in another embodiment; and from about 25° C. to about 270° C. in still another embodiment; and from about 80° C. to about 250° C. in another embodiment, and generally, the curing time may be chosen between about 1 minute to about 6 hours in one embodiment, between about 5 minutes to about 4 hours in another embodiment, and between about 10 minutes to about 2 hours in still another embodiment. Below a period of time of about 1 minute, the time may be too short to ensure sufficient reaction under conventional processing conditions; and above about 4 hours, the time may be too long to be practical or economical.

In another embodiment, the curable resin composition can be cured using a UV curing mechanism under UV curing conditions. For example, the curing of a curable composition of the present invention containing a UV photoinitiator may be carried out under a predetermined amount of UV light source and for a predetermined period of time sufficient to cure the composition; and the curing conditions may be dependent on the photoinitiator used in the formulation. An example of a UV formulation is described above. UV curing is generally conducted at an ambient temperature of 10-35° C., although heat may be applied (for example with infrared lamps) to finish the cure thermally.

The cured product (i.e. the cross-linked product made from the curable composition) of the present invention shows several improved properties over conventional epoxy cured resins. For example, the cured product of the present invention may advantageously have a high glass transition temperature (Tg).

For example, the cured product of the present invention exhibits a glass transition temperature generally of between about 50° C. and about 350° C. in one embodiment, between about 80° C. and about 300° C. in another embodiment. The Tg of the cured product can be measured by differential scanning calorimetry or dynamic mechanical analysis.

The curable composition of the present invention may be used to manufacture a cured thermoset product. For example, the curable composition may be used in applications including electronic applications such as capillary underfill formulations and electrically conductive adhesive formulations. The curable composition of the present invention may be also used as clean resin or clean reactive diluent for electronic applications or as a reactive diluent for composite applications, electrically conductive adhesive (ECA) formulations, and for UV cure applications (i.e. coatings), UV cure formulations for inks and coatings, and laminate applications. Other additional coatings applications may be possible as well. The curable composition of the present invention may also be used in, but not limited to, solder masks, conductive inks, and adhesives.

For example, the low viscosity epoxide resin compound of the present invention is useful as a component in a liquid coating formulation. Typical formulations and processes for such uses are described for example in Clayton A. May, "Epoxy Resins Chemistry & Technology", $2^{nd}$ Edition, Marcel Dekker, 1988, pp 735-748 and pp 758-782, incorporated herein by reference. In one embodiment, for example, the epoxy resin is blended with a hardener such as an amine, amide, or an anhydride optionally in the presence of a catalyst, accelerator, fillers, pigments, dyes, wetting agents, surface modifiers, viscosity modifiers, and any other additives to improve the film quality and appearance. The low viscosity epoxide resin compound of the present invention makes such epoxide resin particularly suitable for solvent-free formulations, but a solvent may optionally be added to the coating formulation if desired.

In another embodiment, the low viscosity epoxide resin compound of the present invention can be useful for photocure (also known as UV-cure) coatings that are used for example as surface coats, solder masks, and coatings for photolithography. The low viscosity epoxide resin compound of the present invention is also useful as a component in ink formulations that are either thermally cured or photocured. A light-sensitive catalyst can be used for photocuring that decomposes to a strong acid when exposed to light. A general description of photocure coating technology is given, for example, in the Clayton A. May reference above at pp 763-766, incorporated herein by reference.

In still another embodiment, the low viscosity epoxide resin compound of the present invention is useful as a component in adhesive formulations. A general description of suitable formulations is given, for example, in the Clayton A. May reference above at pp 683-693, incorporated herein by reference. In addition the low viscosity epoxide resin compound of the present invention is useful for underfill adhesives for semiconductor packaging.

In still another embodiment, the low viscosity epoxide resin compound of the present invention is useful for electrical and electronic applications such as for example electrical potting and encapsulation and using processes such as casting, impregnation, and resin transfer molding. A description of typical formulations and processes for such uses is given, for example, in the Clayton A. May reference above at pp 790-813, incorporated herein by reference.

In still another embodiment, the low viscosity epoxide resin compound of the present invention is useful for printed circuit board applications such as for example electrical laminates. It can be used in, but it's use is not limited to applications such as high density interconnect formulations, and pre-pregs, copper clad laminates, and low dk/df formulations for servers and routers.

EXAMPLES

The following examples and comparative examples further illustrate the present invention in detail but are not to be construed to limit the scope thereof.

Various terms and designations used in the following examples are explained herein below:

"DVHPTO" stands for divinylhexahydropentalene trioxide also known as 2,4-di(oxiran-2-yl)octahydropentaleno[1,2-b]oxirene and as illustrated in Structure (I) above.

"DVHP" stands for divinyl hexahydro pentalene, also called 2,4-divinylbicyclo[3.3.0]oct-6-ene also called 1,3-divinyl-1,2,3,3a,4,6a-hexahydropentalene.

"IPDA" stands for isophoronediamine.

"PACM" stands for 4,4'-methylenebis-cyclohexanamine

ECA100 refers to Epoxy Curing Agent 100. ECA100 is an anhydride hardener that is commercially available from Dixie Chemical Company, Inc.; and is composed of methyltetrahydrophthalic anhydride and tetrahydrophthalic anhydride.

"DVBDO" stands for divinylbenzene dioxide.

EMI-24-CN is 1-(2-cyanoethyl)-2-ethyl-4(5)-methylimidazole and commercially available from PCI Synthesis.

"2-MI" stands for 2-methyl imidazole.

UVI 6992 is a product containing approximately 55 wt % propylene carbonate and approximately 45 wt % mixed triaryl sulfonium salts; and is commercially available from Aceto Corp.

Xiameter® OFS-6040 is an epoxy-functionalized trimethoxy silane commercially available from Dow Corning.

Jeffamine® D230 is a difunctional polyetheramine commercially available from Huntsman.

MP8FS Silica is a silica particles product having a mean particle size of 0.7 µm; and MP15EF Silica is a silica particles product having a mean particle size of 1.1 µm; both products which are commercially available from Tatsumori.

D.E.R. 354 is bisphenol F diglycidylether resin having an EEW of about 170; D.E.R 383 is bisphenol A diglycidyl ether resin having an EEW of about 180 g/equivalent; and D.E.R. 560 is a brominated epoxy resin; all products which are commercially available from The Dow Chemical Company.

Epodil® 749 is a reactive diluent, which is the diglycidyl ether of neopentyl glycol; Epodil® 750 is the diglycidyl ether of 1,4-butanediol; and Epodil® 757 is the glycidyl ether of cyclohexane dimethanol; all products of which are commercially available from Air Products.

EpiClon 830 LVP is high purity bisphenol F epoxy resin available from DIC Corp.

Kayahard AA is 4,4'-methylenebis-(2-ethylaniline) available from Nippon Kayaku.

SMA EF-40 is a styrene-maleic anhydride copolymer with a styrene:maleic anhydride ratio of approximately 4:1 and is commercially available from Cray Valley.

Byk®-W 996 and Byk A530 are both wetting and dispersing agent available from Byk Chemie.

The following standard analytical equipment and methods are used in the Examples:

Glass Transition Temperature

For examples 1-3 and comparative examples A-F, Tg was obtained via Dynamic Mechanical Thermal Analysis. For the analysis, a three-point bend test was used to collect tan delta data. Samples were approximately 12.5 mm wide and 12 mm long. The samples were then measured with a caliper, placed on the 10 mm 3-Point Bend Fixture of the TA Instruments RSA III Rheometer and tested in a closed oven with a constant nitrogen flow. A dynamic temperature ramp was performed: samples were measured with an oscillatory test (1 Hz) along a temperature ramp (5° C./minute) starting from room temperature and stopping at 300° C. Tg was reported as peak tan delta.

Viscosity

Viscosities were collected using an AR2000EX stress controlled rheometer (TA Instruments) with cone-and-plate geometry (stainless steel 40 mm, 2° cone, 51 micron truncation gap). A shear rate of 10 $sec^{-1}$ is used for these measurements. After equilibrating at 25° C. for 30 s, the temperature is ramped from 25° C. to 90° C. at a rate of 2° C./minute, with 10 points collected per decade. Temperature control is achieved with a Peltier plate and water bath circulator.

Glass Slide Test Vehicle to Collect Flow Time

A glass slide flow test vehicle is constructed by placing 2 pieces of 50 µm thick tape onto opposite sides of a glass slide. A cover slip is placed on top of the tape to create a 50 µm gap and the cover slip is taped in place. Underfill is applied along one side of the cover slip and the time it takes to fill the area under the glass cover slip is recorded as the flow time.

Thermogravimetric Analysis (TGA)

To determine weight loss during cure, a 40 mg (+/−1 mg) sample was placed in a TGA pan and ramped to 150° C. at a rate of 10° C./minute and held isothermally at that temperature for 20 minutes.

Dynamic Scanning Calorimetry (DSC)

To obtain Tg for Example 8 and Comparative Examples H-K, a TA Instruments Q2000 DSC was used to measure glass transition temperatures ($T_g$). The uncured sample was placed in a DSC pan and then the $T_g$ was measured using the following method:

1: Ramp 10° C./minute to 250° C.,
2: Isothermal for 10 minutes,

3: Equilibrate at 25° C., and
4: Ramp 10° C./minute to 220° C.

The $T_g$ was found using the half-extrapolated tangents method on the data from the second thermal ramp. Data from the first thermal ramp was discarded.

Examples 1-3

Synthesis of Curable Compositions and Thermosets and Comparative Examples A-F

Several thermosets were prepared with various concentrations of the components described in Table I as follows: The compounds in each of the examples described in Table I were thoroughly mixed together to form a resin mixture. Each one of the resin mixtures of Table I were separately coated onto a 10 cm by 10 cm piece of interwoven glass cloth. Then the resultant coated cloth was cured in an oven at 100° C. for 1 hour, followed by a post-cure at 220° C. for 2 hours.

TABLE I

| | COMPONENTS | | | | | | |
|---|---|---|---|---|---|---|---|
| EXAMPLE | DVHPTO (g) | IPDA (g) | PACM (g) | ECA100 (g) | DVBDO (g) | D.E.R. 354 (g) | EMI-24-CN (g) |
| Example 1 | 0.63 | 0.37 | | | | | |
| Example 2 | 2.33 | | 1.67 | | | | |
| Example 3 | 0.40 | | | 0.59 | | | 0.01 |
| Comparative Example A | | 10.00 | | | 5.00 | | |
| Comparative Example B | | | 2.67 | | 4.33 | | |
| Comparative Example C | | | | 3.28 | 4.64 | | 0.08 |
| Comparative Example D | | 1.43 | | | | 6.09 | |
| Comparative Example E | | | 1.67 | | | 5.84 | |
| Comparative Example F | | | | 1.46 | | 4.48 | 0.06 |

The glass transition temperature for the cured formulations in Examples 1-3 and Comparative Examples A-F were collected using the dynamic mechanical analysis method described above. The data are illustrated in Table II below.

TABLE II

| | EPOXY | | |
|---|---|---|---|
| HARDENER | Examples 1-3 DVHPTO Tg (° C.) | Comparative Examples A-C DVBDO Tg (° C.) | Comparative Examples D-F D.E.R. 354 Tg (° C.) |
| IPDA | 223 | 227 | 118 |
| PACM | 261 | 228 | 122 |
| ECA100 | 250 | 115 | 111 |

Examples 4 and 5

Thermosets for UV Coatings

DVHPTO and UVI 6992 catalyst were combined in accordance with the weights shown in Table III; and then the mixture was applied to Bonderite steel panels as a film having a thickness of 12 microns. The panels were UV processed using a 240 W/cm mercury bulb to form a coating. The formulations cured to give coated panels.

TABLE III

| Compound | Example 4 (g) | Example 5 (g) |
|---|---|---|
| DVHPTO | 10.05 | 8.29 |
| UVI 6992 Catalyst | 0.057 | 0.17 |

Example 6

Thermoset for Underfill Adhesive

DVHPTO, silica, and carbon black were added to a polyethylene FlackTek™ speed mixing container and mixed using a FlackTek™ DAC150 speed mixer for 30 seconds (s) at 2500 revolutions per minute (rpm). Xiameter® OFS-6040 silane (1.1 wt % on silica) was added to the FlackTek™ DAC150 speed mixer; and the resulting sample was mixed for 30 s at 2500 rpm. Jeffamine® D230 was added to the sample and then the sample was further mixed for 30 s at 2500 rpm. The sample was roll-milled using a 3 roll mill. The weight of IPDA was re-calculated to account for material losses during roll milling and then the IPDA was added to the sample. The sample was mixed again at 2500 rpm for 30 s and then degassed for 15 minutes under vacuum in a bell jar. The weight percent of each component is described in Table IV.

TABLE IV

| Component | Weight % of Component |
|---|---|
| IPDA | 3.27 |
| DVHPTO | 26.15 |
| Jeffamine ® D230 | 9.81 |
| MP8FS Silica | 60.00 |
| Xiameter OFS- 6040 silane | 0.66 |
| Carbon black | 0.12 |

Comparative Example G

EpiClon EXA 830-LVP and silica were added to a polyethylene FlackTek™ speed mixing container and mixed using a FlackTek™ DAC150 speed mixer for 30 s at 2500 rpm. Xiameter® OFS-6040 silane (1.1 wt % on silica) was added and the sample was mixed for 30 s at 2500 rpm. Byk®-W 996 was added and the sample mixed for 30 s at 2500 rpm. Byk® A530 was added and the sample mixed for 30 s at 2500 rpm. Kayahard AA was then added and the sample mixed for 30× at 2500 rpm. The sample was then degassed for 15 minutes under vacuum in a bell jar. The weight percent of each component is listed in Table V.

TABLE V

| Component | Weight % Component |
|---|---|
| EpiClon 830LVP | 36.46 |
| Kayahard AA | 12.54 |
| MP15EF | 50.00 |
| Xiameter ® OFS- 6040 silane | 0.55 |
| Byk W-996 | 0.20 |
| Byk A530 | 0.25 |

The properties of the underfill from Example 6 were measured and are shown in Table VI. The viscosity of the underfill from Example 6 is lower relative to the control formulation and the flow time is faster.

TABLE VI

| Property | Comparative Example G | Example 6 |
|---|---|---|
| Viscosity (Pa·s) at 25° C. | 8.01 | 1.45 |
| Viscosity (Pa·s) at 85° C. | 0.10 | 0.09 |
| Tg After Cure (° C.) | 91 | 115 |
| Flow Time (s) | 72 | 33 |

Example 7

Reactive Diluent for Electronics

DVHPTO was added to D.E.R. 383 at various weight percents as described in Table VII. DVHPTO was shown to decrease the viscosity of the epoxy resin D.E.R. 383 as shown in Table VII.

TABLE VII

| | % DVHPTO in D.E.R. 383 | | | | | | |
|---|---|---|---|---|---|---|---|
| | 0 | 5 | 10 | 15 | 20 | 30 | 40 |
| Viscosity (Pa·s) | 9.2 | 7.2 | 5.8 | 4.8 | 3.9 | 2.6 | 1.6 |

Example 8

Reactive Diluent for Electronics

A formulation to investigate epoxy homopolymerization of D.E.R 383 with 1-methylimidazole as a catalyst and DVHPTO as a reactive diluent was prepared. The reagents in Table VIII were added to a polyethylene FlackTek™ speed mixing container and mixed for 30 s at 2500 rpm to prepare a homogeneous solution.

TABLE VIII

| Component | Example 8 |
|---|---|
| D.E.R. 383 | 81.6 |
| DVHPTO | 14.4 |
| 1-methylimidazole | 4.0 |

Comparative Examples H-K

Comparative formulations were prepared to investigate epoxy homopolymerization of D.E.R 383 with 1-methylimidazole as a catalyst and other reactive diluents. D.E.R. 383 (8.16 g), the diluent in Table IX (1.4 g) and 1-methylimidazole (0.4 g) were added to a polyethylene FlackTek™ speed mixing container and mixed for 30 s at 2500 rpm to prepare a homogeneous solution.

TABLE IX

| Comparative Example | Diluent |
|---|---|
| Example H | Control, no diluents included |
| Example I | Epodil ® 757 (CHDM-DGE) |
| Example J | Epodil ® 750 (BD-DGE) |
| Example K | Epodil ® 749 (NPG-DGE) |

The samples were analyzed for viscosity, Tg, and weight loss and the resulting data is described in Table X. DVHPTO decreases the viscosity of the resin and increases Tg.

TABLE X

| Resin Type | Viscosity @ 25° C. (Pa·s) | $T_g$ (° C.) | Weight Loss During Cure (%) |
|---|---|---|---|
| Control - no diluents (Comparative Example H) | 9.2 | 145 | 1.2 |
| DVHPTO (Example 7) | 4.8 | 164 | 2.7 |
| Epodil ® 757 (CHDM-DGE) (Comparative Example I) | 2.5 | 125 | 2.4 |
| Epodil ® 750 (BD-DGE) (Comparative Example J) | 1.2 | 118 | 3.1 |
| Epodil ® 749 (NPG-DGE) (Comparative Example K) | 1.7 | 118 | 4.3 |

Example 9

Electrical Laminates

D.E.R. 560 in (60% in MEK), SMA-EF-40 (60% in MEK), DVHPTO, and 2-MI (20% in Dowanol PM) were weighed into a 200 mL jar and placed on a shaker until a homogeneous mixture was obtained. The weights used for the formulation are shown in Table XI. An epoxy/hardener ratio of 1.0 was used.

TABLE XI

| Reagents | EEW | Solids Weight | Solution Weights (g) |
|---|---|---|---|
| DER 560 (60% in MEK) | 455 | 31.2 | 52.0 |
| SMA EF-40 (60% in MEK) | 513 | 63.3 | 105.5 |
| DVHPTO | 104 | 5.7 | 5.7 |
| 2-MI (20% in Dowanol PM) | | 0.6 | 0.6 |

Comparative Example L

D.E.R. 560 in (60% in MEK), SMA-EF-40 (60% in MEK), and 2-MI (20% in Dowanol PM) were weighed into a 200 mL jar and placed on a shaker until a homogeneous mixture was obtained. The weights used for the formulation are shown in Table XII.

TABLE XII

| Reagents | EEW | Solids Weight (g) | Solution Weights (g) |
|---|---|---|---|
| DER 560 (60% in MEK) | 455 | 47.0 | 78.3 |
| SMA EF-40 (60% in MEK) | 513 | 53.0 | 88.3 |
| 2-MI (20% in Dowanol PM) | | 0.6 | 0.6 |

The above formulations from Example 9 and Comparative Example L were gelled at 171° C. on a hot plate. The gelled samples were then post-cured for 2 hours at 200° C. in an oven. The cured samples were analyzed for Tg and the resulting data is shown in Table XIII. DVHPTO was shown to increase Tg.

TABLE XIII

| Resin Type | Tg (° C.) |
|---|---|
| Example 9 with DVHPTO | 168 |
| Comparative Example L | 158 |

The invention claimed is:

1. A curable composition comprising at least one low viscosity epoxide resin compound having the following chemical structure:

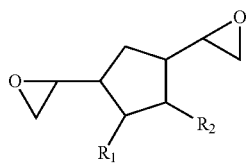

wherein $R_1$ and $R_2$ are both a group having from 1 to 20 carbon atoms.

2. The curable composition of claim 1, including at least one curing agent.

3. The curable composition of claim 2, wherein the at least one curing agent comprises an anhydride, a carboxylic acid, an amine compound, a phenolic compound, a cyanate ester or mixtures thereof.

4. The curable composition of claim 2, wherein the concentration of the at least one curing agent is from about 5 weight percent to about 95 weight percent of the curable composition.

5. The curable composition of claim 1, including at least one UV photoinitiator.

6. The curable composition of claim 5, wherein the at least one UV photoinitiator comprises diaryliodonium salts, phenacylsulfonium salts, and mixtures thereof.

7. The curable composition of claim 5, wherein the concentration of the at least one UV photoinitiator is from about 0.01 weight percent to about 10 weight percent of the curable composition.

8. The curable composition of claim 1, including a catalyst, a second epoxide compound separate and different from the at least one low viscosity epoxide resin compound (a), a filler, a reactive diluent, a flexibilizing agent, a processing aide, a toughening agent, a solvent, a reinforcing material, or a mixture thereof.

9. The curable composition of claim 1, wherein $R_1$ and $R_2$ of the epoxide resin compound are both a hydrocarbon group having from 1 to 5 carbon atoms.

10. The curable composition of claim 1, wherein $R_1$ and $R_2$ of the epoxide resin compound are bonded together to form a cycloalkane with a bridging group having from 1 to about 8 carbon atoms.

11. The curable composition of claim 1, wherein $R_1$ and $R_2$ of the epoxide resin compound are bonded together to form a cycloalkane group having from 1 to about 8 carbon atoms.

12. The curable composition of claim 1, wherein $R_1$ and $R_2$ of the epoxide resin compound are both a hydrocarbon group having from 1 to about 20 carbon atoms, and wherein the $R_1$ and/or the $R_2$ group includes an oxirane group.

13. The curable composition of claim 1, wherein $R_1$ and $R_2$ of the epoxide resin compound are bonded together to form a cycloalkane group having from 1 to about 20 carbon atoms, and wherein an oxirane group is attached to the ring.

14. The curable composition of claim 1, wherein $R_1$ and $R_2$ of the epoxide resin compound are bonded together to form a cycloalkane with a bridging group having from 1 to about 8 carbon atoms; and wherein the $R_1$ and/or the $R_2$ group includes an oxirane group.

15. The curable composition of claim 1, wherein the at least one low viscosity epoxide resin compound comprises divinylhexahydropentalene trioxide having the following chemical structure:

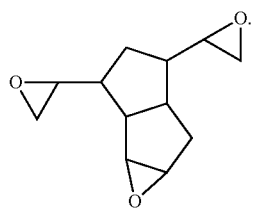 [SMILES: C1OC1C1CC(C2CO2)C2C1CC1OC12]

16. The curable composition of claim 1, wherein the at least one low viscosity epoxide resin compound comprises a compound having the following chemical structure:

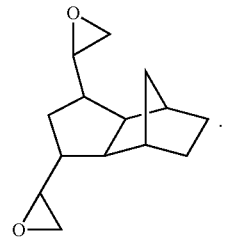 [SMILES: C1CC2CC1C1C(C3CO3)CC(C3CO3)C21]

17. The curable composition of claim 1, wherein the at least one low viscosity epoxide resin compound has a viscosity of less than about 1 Pa-s.

18. The curable composition of claim 1, wherein the concentration of the at least one low viscosity epoxide resin compound is from about 1 weight percent to about 99.5 weight percent of the curable composition.

19. A process for preparing a curable composition comprising admixing: (a) at least one low viscosity epoxide resin compound comprising an epoxide compound having the following chemical structure:

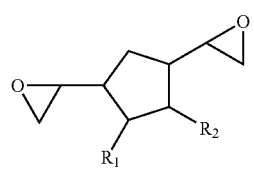

wherein $R_1$ and $R_2$ are both a hydrocarbon group having from 1 to about 20 carbon atoms; (b) at least one curing agent; and (c) optionally, at least one catalyst.

20. A process for preparing a composition comprising:
(I) providing a mixture of:
(a) at least one low viscosity epoxide resin compound comprising an epoxide compound having the following chemical structure:

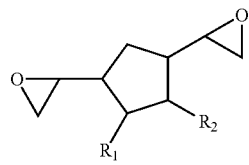

wherein $R_1$ and $R_2$ are both a hydrocarbon group having from 1 to about 20 carbon atoms;
(b) at least one curing agent; and
(c) optionally, at least one catalyst; and
(II) curing the curable composition of step (I).

21. The process of claim 20, wherein the curing step (II) is carried out at a temperature of from about 10° C. to about 325° C.

22. A cured thermoset article prepared by the process of claim 20.

23. The thermoset of claim 22, wherein the thermoset is selected from the group consisting essentially of an adhesive, a composite, an electrical laminate, a coating, a potting compound, an encapsulant, and a capillary underfill.

* * * * *